(12) United States Patent
Huang (10) Patent No.: US 11,197,620 B2
(45) Date of Patent: Dec. 14, 2021

(54) PPG SIGNAL COLLECTION METHOD AND APPARATUS

(71) Applicant: Huawei Technologies Co., Ltd., Shenzhen (CN)

(72) Inventor: Bangyu Huang, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 383 days.

(21) Appl. No.: 16/304,050

(22) PCT Filed: Mar. 20, 2017

(86) PCT No.: PCT/CN2017/077370
§ 371 (c)(1),
(2) Date: Nov. 21, 2018

(87) PCT Pub. No.: WO2017/202120
PCT Pub. Date: Nov. 30, 2017

(65) Prior Publication Data
US 2020/0315475 A1    Oct. 8, 2020

(30) Foreign Application Priority Data
May 26, 2016  (CN) .......................... 201610363677.0

(51) Int. Cl.
*A61B 5/024* (2006.01)
*A61B 5/00* (2006.01)
*A61B 5/1455* (2006.01)

(52) U.S. Cl.
CPC ........ *A61B 5/02433* (2013.01); *A61B 5/7203* (2013.01); *A61B 5/7221* (2013.01);
(Continued)

(58) Field of Classification Search
CPC . A61B 5/02433; A61B 5/7203; A61B 5/7221; A61B 5/7246; A61B 5/14552; A61B 2562/0238
See application file for complete search history.

(56) References Cited

U.S. PATENT DOCUMENTS 8,948,832 B2    2/2015 Hong et al.
10,433,739 B2 * 10/2019 Weekly .............. A61B 5/02433
(Continued)

FOREIGN PATENT DOCUMENTS

CN        103156591        6/2013
CN        104224144        12/2014
(Continued)

*Primary Examiner* — Lindsey G Wehrheim
(74) *Attorney, Agent, or Firm* — Slater Matsil, LLP (57) ABSTRACT

The present disclosure relates to a PPG signal collection method and apparatus. The method includes: collecting, by using a light sensor, a first PPG detection signal formed by a first light source, where the first light source is a green light source; collecting, by using the light sensor, a second PPG detection signal formed by a second light source, where the second light source is a red light source; further, determining, according to the first PPG detection signal, whether the first light source meets a preset collection indicator; if the first light source meets the collection indicator, determining, according to the second PPG detection signal, whether the second light source meets the collection indicator; and if the second light source meets the collection indicator, collecting, by using the light sensor, a PPG signal formed by the second light source.

22 Claims, 6 Drawing Sheets

(52) U.S. Cl.
CPC ........ *A61B 5/7246* (2013.01); *A61B 5/14552* (2013.01); *A61B 2562/0238* (2013.01)

(56) References Cited

U.S. PATENT DOCUMENTS

| | | |
|---|---|---|
| 2015/0025394 A1 | 1/2015 | Hong et al. |
| 2015/0201853 A1 | 7/2015 | Hong et al. |
| 2016/0081567 A1 | 3/2016 | Nousiainen et al. |
| 2016/0113526 A1 | 4/2016 | Nageshwar et al. |

FOREIGN PATENT DOCUMENTS

| | | |
|---|---|---|
| CN | 105208924 | 12/2015 |
| CN | 105286845 | 2/2016 |
| WO | 2015102588 | 7/2015 |
| WO | 2016040263 | 3/2016 |

\* cited by examiner

PPG SIGNAL COLLECTION METHOD AND APPARATUS

CROSS-REFERENCE TO RELATED APPLICATIONS

This application is a National Stage of International Application No. PCT/CN2017/077370, filed on Mar. 20, 2017, which claims priority to Chinese Patent Application No. 201610363677.0, filed on May 26, 2016. Both of the aforementioned applications are hereby incorporated by reference in their entireties.

TECHNICAL FIELD

The present invention relates to the communications field, and in particular, to a PPG (Photo Plethysmo Graphy, photoplethysmography) signal collection method and apparatus.

BACKGROUND

A PPG technology is a non-invasive detection technology that is used to detect a change of a blood volume in a living tissue by photoelectric means. When a light beam of a particular wavelength reaches a skin surface of a tested user, the light beam is transferred to a light sensor in a transmission or reflection manner. During this process, a blood volume in a blood vessel fluctuates because of contraction and expansion of a heart. Therefore, when the heart contracts, the blood volume of a peripheral vessel of the heart increases, a light absorption amount also rises, and a light intensity detected by the light sensor is relatively low; when the heart expands, the blood volume of the peripheral vessel of the heart decreases, and the light intensity detected by the light sensor is relatively high. It can be learned that, the light intensity detected by the light sensor pulsates, and a light intensity change signal may be converted to a digitized electrical signal, that is, a PPG signal is obtained.

Further, according to the PPG signal, physiological parameter information such as blood pressure, blood oxygen, cerebral oxygen, muscle oxygen, blood glucose, a pulse rate, and a respiratory rate of the tested user can be obtained. Therefore, most prior-art wearable devices use the foregoing principle to track a health state of a user.

When a green light source is used to collect a PPG signal, the PPG signal obtained has relatively good signal quality. For example, a ripple component is obvious in the collected PPG signal. Therefore, the green light source is disposed on most wearable devices to collect a PPG signal. However, green light needs a relatively large drive current when serving as a light source, leading to relatively high power consumption of a wearable device. Therefore, how to ensure signal quality of a PPG signal while reducing power consumption of a wearable device during PPG signal collection becomes a problem to be resolved urgently.

SUMMARY

Embodiments of the present invention provide a PPG signal collection method and apparatus, so as to select light sources of different features to collect a PPG signal. This reduces power consumption in PPG signal collection while ensuring signal quality of the PPG signal.

To achieve the foregoing objective, the following technical solutions are used in the embodiments of the present invention.

According to a first aspect, an embodiment of the present invention provides a PPG signal collection method, including: collecting, by using a light sensor, a first PPG detection signal formed by a first light source, where the first light source is a green light source or a blue light source; collecting, by using the light sensor, a second PPG detection signal formed by a second light source, where the second light source is a red light source or an infrared light source; further, determining, according to the first PPG detection signal, whether the first light source meets a preset collection indicator; if the first light source meets the collection indicator, determining, according to the second PPG detection signal, whether the second light source meets the collection indicator; and if the second light source meets the collection indicator, collecting, by using the light sensor, a PPG signal formed by the second light source.

It can be learned that, because an application scope is relatively wide when the green light source is used to collect a PPG signal, it may be first determined, according to the first PPG detection signal, that the first light source meets the collection indicator, that is, it is first ensured that the first light source can provide a PPG signal of relatively good signal quality for a tested user. Further, when the first light source meets the collection indicator, it is determined, according to the second PPG detection signal, whether the second light source meets the collection indicator, that is, it is determined whether the red light source or the infrared light source can provide a PPG signal of relatively good signal quality. If the second light source meets the collection indicator, the second light source is also applicable to a PPG signal collection process. In this case, to reduce power consumption of a PPG signal collection apparatus, the first light source may be turned off, and a PPG signal formed by the second light source that consumes less power may be collected by using the light sensor.

In a possible design, a light intensity sensing range of the light sensor is (X, Y), where $0 \leq X < Y$. In this case, a method for determining, according to the first PPG detection signal, whether the first light source meets the collection indicator includes: if a light intensity indicated by the first PPG detection signal lies between a first threshold and a second threshold (the first threshold is greater than the second threshold), determining that the first light source meets the collection indicator; if the light intensity indicated by the first PPG detection signal reaches the first threshold, increasing a maximum value Y of the light intensity sensing range, until the light intensity indicated by the first PPG detection signal lies between the first threshold and the second threshold; or if the light intensity indicated by the first PPG detection signal reaches the second threshold, decreasing a minimum value X of the light intensity sensing range, until the light intensity indicated by the first PPG detection signal lies between the first threshold and the second threshold.

Alternatively, a method for determining, according to the first PPG detection signal, whether the first light source meets the collection indicator includes: calculating a signal-to-noise ratio of the first PPG detection signal; and if the signal-to-noise ratio of the first PPG detection signal lies within a preset signal-to-noise ratio interval, determining that the first light source meets the collection indicator; or if the signal-to-noise ratio of the first PPG detection signal does not lie within the signal-to-noise ratio interval, adjusting a light intensity of the first light source, until the signal-to-noise ratio of the first PPG detection signal lies within the signal-to-noise ratio interval.

In this way, the light intensity of the first light source is adjusted, or the light intensity sensing range of the light sensor is adjusted to determine the first light source that meets the collection indicator, thereby ensuring that the first light source can provide a PPG signal of relatively good signal quality for the tested user.

In a possible design, the determining, according to the second PPG detection signal, whether the second light source meets the collection indicator includes: calculating a signal-to-noise ratio of the second PPG detection signal; and if the signal-to-noise ratio of the second PPG detection signal lies within the preset signal-to-noise ratio interval, determining that the second light source meets the collection indicator; or if the signal-to-noise ratio of the second PPG detection signal does not lie within the signal-to-noise ratio interval, adjusting a light intensity of the second light source, until the signal-to-noise ratio of the second PPG detection signal lies within the signal-to-noise ratio interval.

In this way, the light intensity of the second light source is adjusted, to ensure that the second light source can provide a PPG signal of relatively good signal quality for the tested user.

In a possible design, before the determining, according to the first PPG detection signal, whether the first light source meets a collection indicator, the method further includes: obtaining a light intensity of ambient light; calculating a first correlation coefficient between the light intensity of the ambient light and the first PPG detection signal, and calculating a second correlation coefficient between the light intensity of the ambient light and the second PPG detection signal; and if both the first correlation coefficient and the second correlation coefficient are greater than a correlation coefficient threshold, turning off the first light source and the second light source.

When the light intensity of the ambient light is relatively large, noise pollution is caused to a light beam emitted by the first light source or the second light source, thereby affecting signal quality of a PPG signal collected by the light sensor. A correlation coefficient between the light intensity of the ambient light and a PPG detection signal may reflect a degree of the noise pollution. Therefore, if both the first correlation coefficient and the second correlation coefficient are greater than the correlation coefficient threshold, it means that the light beams emitted by both the first light source and the second light source are polluted by the ambient light. In this case, the signal quality of the collected PPG signal is relatively poor. Therefore, to reduce power consumption in PPG signal collection, the first light source and the second light source may be turned off, and a PPG signal collection function may be turned off.

In a possible design, after the collecting, by using the light sensor, a PPG signal formed by the second light source, the method further includes: establishing a correspondence between light source information of the second light source and an identity of a tested user, for the light sensor to subsequently collect a PPG signal for the tested user according to the light source information of the second light source, where the light source information of the second light source includes the light intensity of the second light source and the light intensity sensing range of the light sensor.

In this way, when the tested user collects a PPG signal again, the light source information of the second light source corresponding to the identity of the tested user may be searched for according to the correspondence, and then the light intensity of the second light source and the light intensity sensing range of the light sensor are set directly according to the light source information of the second light source, and the PPG signal is collected for the tested user. This greatly shortens a time consumed in PPG signal collection.

According to a second aspect, an embodiment of the present invention provides a PPG signal collection apparatus, including a processor, and a light sensor and a memory that are separately connected to the processor.

The light sensor is configured to: collect a first PPG detection signal formed by a first light source, where the first light source is a green light source or a blue light source; and collect a second PPG detection signal formed by a second light source, where the second light source is a red light source or an infrared light source. The processor is configured to: determine, according to the first PPG detection signal, whether the first light source meets a preset collection indicator; if the first light source meets the collection indicator, determine, according to the second PPG detection signal, whether the second light source meets the collection indicator; and if the second light source meets the collection indicator, collect, by using the light sensor, a PPG signal formed by the second light source.

In a possible design, a light intensity sensing range of the light sensor is (X, Y), where $0 \leq X < Y$. The processor is specifically configured to: if a light intensity indicated by the first PPG detection signal lies between a first threshold and a second threshold, determine that the first light source meets the collection indicator, where the first threshold is greater than the second threshold.

In a possible design, the processor is further configured to: if the light intensity indicated by the first PPG detection signal reaches the first threshold, increase a maximum value Y of the light intensity sensing range, until the light intensity indicated by the first PPG detection signal lies between the first threshold and the second threshold; or if the light intensity indicated by the first PPG detection signal reaches the second threshold, decrease a minimum value X of the light intensity sensing range, until the light intensity indicated by the first PPG detection signal lies between the first threshold and the second threshold.

In a possible design, the processor is specifically configured to: calculate a signal-to-noise ratio of the first PPG detection signal; and if the signal-to-noise ratio of the first PPG detection signal lies within a preset signal-to-noise ratio interval, determine that the first light source meets the collection indicator.

In a possible design, the processor is further configured to: if the signal-to-noise ratio of the first PPG detection signal does not lie within the signal-to-noise ratio interval, adjust a light intensity of the first light source, until the signal-to-noise ratio of the first PPG detection signal lies within the signal-to-noise ratio interval.

In a possible design, the processor is specifically configured to: calculate a signal-to-noise ratio of the second PPG detection signal; and if the signal-to-noise ratio of the second PPG detection signal lies within the preset signal-to-noise ratio interval, determine that the second light source meets the collection indicator.

In a possible design, the processor is further configured to: if the signal-to-noise ratio of the second PPG detection signal does not lie within the signal-to-noise ratio interval, adjust a light intensity of the second light source, until the signal-to-noise ratio of the second PPG detection signal lies within the signal-to-noise ratio interval.

In a possible design, the light sensor is further configured to obtain a light intensity of ambient light; and the processor is further configured to: calculate a first correlation coefficient between the light intensity of the ambient light and the first PPG detection signal, and calculate a second correlation coefficient between the light intensity of the ambient light and the second PPG detection signal; and if both the first correlation coefficient and the second correlation coefficient are greater than a correlation coefficient threshold, turn off the first light source and the second light source.

In a possible design, the processor is further configured to: establish a correspondence between light source information of the second light source and a tested user, and save the correspondence to the memory, where the light source information of the second light source includes the light intensity of the second light source and the light intensity sensing range of the light sensor.

According to a third aspect, an embodiment of the present invention provides a computer storage medium, configured to store computer software instructions used by the foregoing PPG signal collection apparatus, including a program designed for a PPG collection apparatus for executing the foregoing aspects.

In the present invention, a name of the foregoing PPG signal collection apparatus does not constitute a limitation on devices or functional modules. In a practical implementation, these devices or functional modules may appear in other names. If a function of a device or a functional module is similar to that in the present invention, the device or the functional module falls within the scope defined by the claims of the present invention and their equivalent technologies.

In addition, for a technical effect brought by any design manner in the second and third aspects, reference may be made to technical effects brought by different design manners in the first aspect. Details are not repeated herein.

These or other aspects of the present invention are more concise and comprehensible in descriptions of the following embodiments.

BRIEF DESCRIPTION OF THE DRAWINGS

To describe the technical solutions in the embodiments of the present invention or in the prior art more clearly, the following briefly describes the accompanying drawings required for describing the embodiments or the prior art.

DETAILED DESCRIPTION OF ILLUSTRATIVE EMBODIMENTS

The following clearly and completely describes the technical solutions in the embodiments of the present invention with reference to the accompanying drawings in the embodiments of the present invention. Apparently, the described embodiments are merely some but not all of the embodiments of the present invention.

In addition, the terms "first" and "second" are merely intended for a purpose of description, and shall not be understood as an indication or implication of relative importance or implicit indication of the number of indicated technical features. Therefore, a feature limited by "first" or "second" may explicitly or implicitly include one or more features. In the descriptions of the present invention, unless otherwise indicated, the meaning of "multiple" is two or more.

The term "and/or" in this specification describes only an association relationship for describing associated objects and represents that three relationships may exist. For example, A and/or B may represent the following three cases: Only A exists, both A and B exist, and only B exists. In addition, the character "/" in this specification generally indicates an "or" relationship between the associated objects.

Specifically, an embodiment of the present invention provides a PPG signal collection method. The method may be applied to a PPG signal collection apparatus (referred to as a collection apparatus in subsequent embodiments). The collection apparatus may be specifically a wearable device, such as a wearable watch or a wearable wristband.

Figure 1:
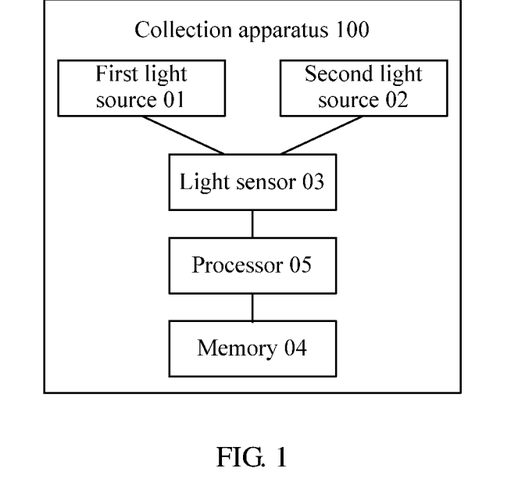
FIG. 1 is a schematic structural diagram of a PPG signal collection apparatus according to an embodiment of the present invention.

Referring to FIG. 1, FIG. 1 is a schematic structural diagram of the collection apparatus 100. The collection apparatus 100 specifically includes a first light source 01, a second light source 02, a light sensor 03, a memory 04, and a processor 05. The processor 05 is connected to both the light sensor 03 and the memory 04. The light sensor 03 may be configured to collect a PPG signal formed by any light source.

The first light source 01 is specifically a green light source or a blue light source. The second light source 02 is specifically a red light source or an infrared light source. For example, the first light source 01 is a blue LED (Light Emitting Diode, light emitting diode), and the second light source 02 is a red LED.

The light sensor 03 is configured to collect a PPG signal formed by the first light source 01 or the second light source 02. Specifically, when a light beam emitted by the first light source 01 or the second light source 02 reaches a skin surface of a tested user, the light beam may be transferred to the light sensor 03 in a transmission or reflection manner. The light sensor 03 may detect a light intensity variation signal of a light beam received by the light sensor 03, and convert the light intensity variation signal to a digitized electrical signal, to obtain a PPG signal. Certainly, the light sensor 03 may further collect a light intensity of ambient light, and the like. This is not limited in this embodiment of the present invention.

Figure 2:
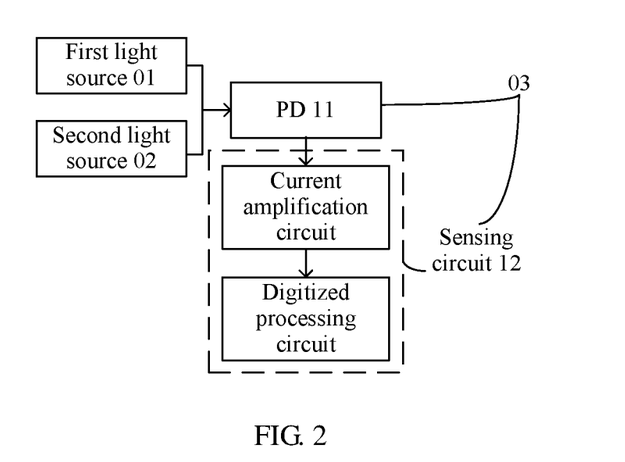
FIG. 2 is a schematic principle diagram 1 of a PPG signal collection apparatus according to an embodiment of the present invention.

For example, as shown in FIG. 2, the light sensor 03 may include a PD 11 (Photo Diode, photodiode) and a sensing circuit 12. The sensing circuit 12 specifically includes a current amplification circuit and a digitized processing circuit. Specifically, the PD 11 of the light sensor 03 detects that a light signal emitted by the first light source 01 or the second light source 02 is converted to a current signal. Further, the sensing circuit 12 of the light sensor 03 amplifies the current signal, and performs digitized processing to obtain a digitized electrical signal (that is, a PPG signal). The PPG signal includes an alternating current component and a direct current component. Optionally, the processor 05 may subsequently further separate the alternating current component from the direct current component in the PPG signal by using a filtering algorithm. The filtering algorithm may be an FFT (Fast Fourier Transformation, a fast algorithm of a discrete fourier transform) digital filtering algorithm, or may be another filtering algorithm. This is not limited in this embodiment of the present invention.

Figure 3:
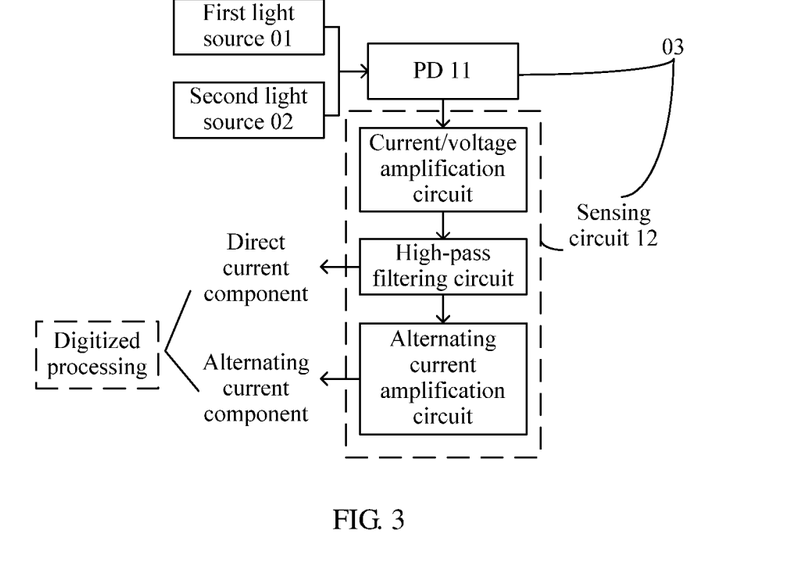
FIG. 3 is a schematic principle diagram 2 of a PPG signal collection apparatus according to an embodiment of the present invention.

Alternatively, a two-stage manner may further be used to directly collect an alternating current component and a direct current component from a PPG signal. In this case, as shown in FIG. 3, the sensing circuit 12 may specifically include a current/voltage amplification circuit, a high-pass filtering circuit, and an alternating current amplification circuit. Specifically, the current/voltage amplification circuit is configured to convert the current signal obtained by the PD 11 to a voltage signal, and amplifies the voltage signal. The high-pass filtering circuit is configured to separate an alternating current component from a direct current component in the voltage signal. The alternating current amplification circuit is configured to amplify the separated alternating current component, so that the separated alternating current component can be used for subsequent digitized processing. In this way, the alternating current component and the direct current component have been separated in the obtained PPG signal, and subsequently digitized processing may be performed separately on the separated alternating current component and direct current component.

The memory 04 is configured to store a correspondence between light source information of each light source and an identity of a tested user. Light source information of the first light source 01 specifically includes a light intensity of the first light source 01 and a light intensity sensing range of the light sensor 03. Light source information of the second light source 02 specifically includes a light intensity of the second light source 02 and the light intensity sensing range of the light sensor 03. An identity of a tested user may be used to indicate different tested users. Therefore, when a same tested user collects a PPG signal by using the collection apparatus 100 not for the first time, the PPG signal may be collected directly according to light source information of a corresponding light source based on the correspondence. This can effectively shorten a time consumed in PPG signal collection. Certainly, a default initial light source (for example, by default, a light source that is used when the collection apparatus 100 is used for the first time is a green light source of a particular light intensity), a default light intensity sensing range of the light sensor, and the like may further be pre-stored in the memory 04. This is not limited in this embodiment of the present invention.

The processor 05 is a control center of the collection apparatus 100, and may be one or more general purpose central processing units, microprocessors, or application-specific integrated circuits (application-specific integrated circuit, ASIC), or one or more integrated circuits for controlling execution of a solution program of the present invention.

Specifically, according to PPG detection signals collected by the light sensor 03 that are formed by different light sources, the processor 05 may set the light intensity sensing range of the light sensor 03, set a type of a light source (that is, the first light source 01 or the second light source 02) used to collect a PPG signal, and set a light intensity of any type of light source. Certainly, the processor 05 may further be configured to control turning on and off of each light source. This is not limited in this embodiment of the present invention.

It should be noted that, different types of light have different absorbance by skin tissue components, such as melanin, protein, $HbO_2$ (oxyhemoglobin, oxyhemoglobin), and Hb (hemoglobin, hemoglobin). Therefore, different types of light sources have different application scopes in PPG signal collection. In other words, when different tested users collect PPG signals by using different types of light sources, the obtained PPG signals may be in different signal quality.

Generally, an application scope of the green light source is relatively wide in PPG signal collection. For most tested users, when the green light source is used to collect a PPG signal, a ripple component of relatively good signal quality can be obtained. In contrast, an application scope of the red light source is relatively narrow in PPG signal collection. When some tested users use the red light source to collect a PPG signal, a ripple component of the obtained PPG signal is not quite obvious. As a result, when the ripple component is subsequently used to detect physiological parameters, such as blood pressure and blood oxygen, of the tested users, an error may occur. However, when serving as a light source, green light requires a relatively large drive current, leading to relatively high power consumption of the collection apparatus; when serving as a light source, red light requires a relatively low drive current, and therefore, power consumption of the collection apparatus is relatively low.

Therefore, for different tested users whose skin tissue components have different absorption, this embodiment of the present invention provides the PPG signal collection method, to select an appropriate light source for a tested user to collect a PPG signal. This can ensure signal quality of the PPG signal and reduce power consumption in PPG signal collection.

Figure 4:
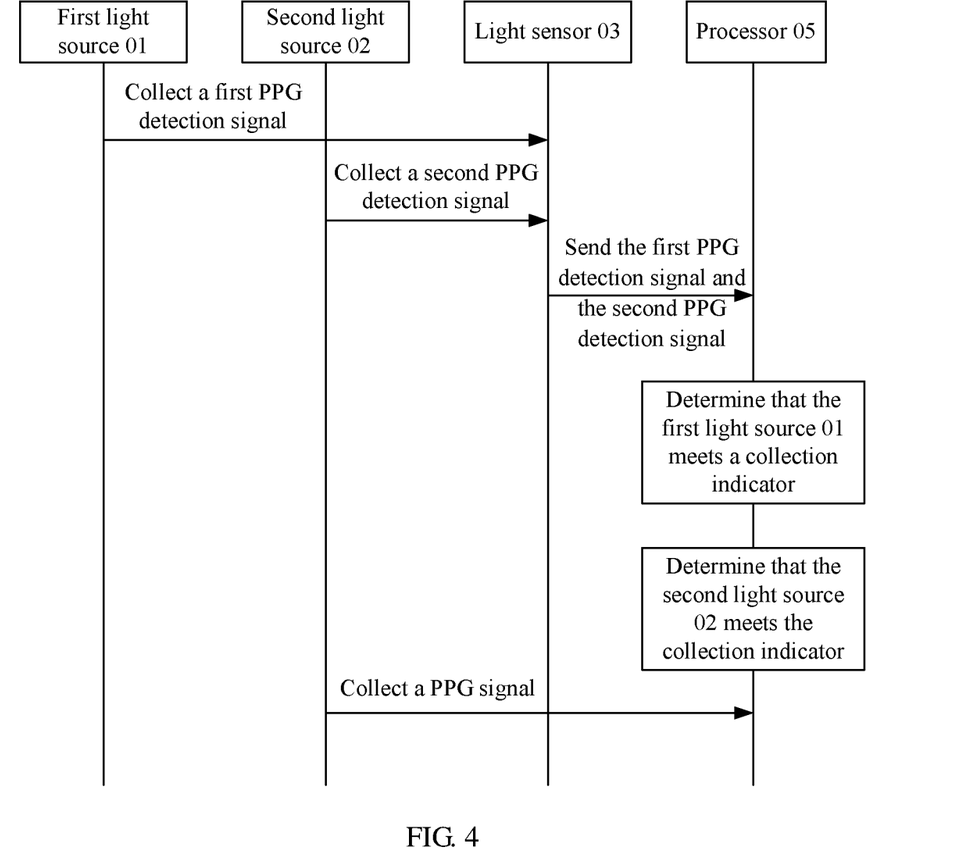
FIG. 4 is a schematic interaction diagram of a PPG signal collection method according to an embodiment of the present invention.

Specifically, as shown in FIG. 4, when a tested user collects a PPG signal by using the collection apparatus for the first time, the first light source 01 may be used by default to collect the PPG signal because an application scope of the first light source 01 (that is, the green light source or the blue light source) is relatively wide in PPG signal collection. In this case, to determine a light source that can be used to collect a PPG signal of relatively good signal quality for the tested user, the light sensor 03 may collect a first PPG detection signal formed by the first light source 01 and a second PPG detection signal formed by the second light source 02. Further, the light sensor 03 sends the first PPG detection signal and the second PPG detection signal to the processor 05. The processor 05 first determines, according to the first PPG detection signal, whether the first light source meets a collection indicator, that is, determines whether the green light source or blue light can provide a PPG signal of relatively good signal quality. Further, after determining that the first light source meets the collection indicator, the processor 05 further determines, according to the second PPG detection signal, whether the second light source meets the collection indicator, that is, determines whether the red light source or the infrared light source can provide a PPG signal of relatively good signal quality. If the second light source meets the collection indicator, it means that a PPG signal of relatively high signal quality can be obtained when the second light source is used. In this case, to reduce power consumption of the collection apparatus, the processor 05 may use the light sensor 03 to collect a PPG signal formed by the second light source 02 that consumes less power.

It can be learned that, because the application scope is relatively wide when the green light source is used to collect the PPG signal, the collection apparatus may first determine, according to the first PPG detection signal, the first light source that meets the collection indicator, that is, first ensure that the first light source can provide a PPG signal of relatively good signal quality for the tested user. Further, when the first light source meets the collection indicator, the collection apparatus determines, according to the second PPG detection signal, whether the second light source meets the collection indicator, that is, determines whether the red light source or the infrared light source can provide a PPG signal of relatively good signal quality. If the second light source meets the collection indicator, it means that the second light source is also applicable to a PPG signal collection process. In this case, to reduce power consumption of the collection apparatus, the first light source may be turned off, and the PPG signal formed by the second light source that consumes less power may be collected by using the light sensor.

Certainly, if the first light source does not meet the collection indicator, because the application scope of the first light source in PPG signal collection is wider than the application scope of the second light source in PPG signal collection, the second light source cannot be used as the light source of the collection apparatus for PPG signal collection, either. In this case, a PPG signal collection function may be turned off.

In addition, if the second light source does not meet the collection indicator, it means that only the first light source is applicable to the PPG signal collection process. In this case, the light source does not need to be switched, and the first light source may continue to be used to collect the PPG signal.

Figure 5:
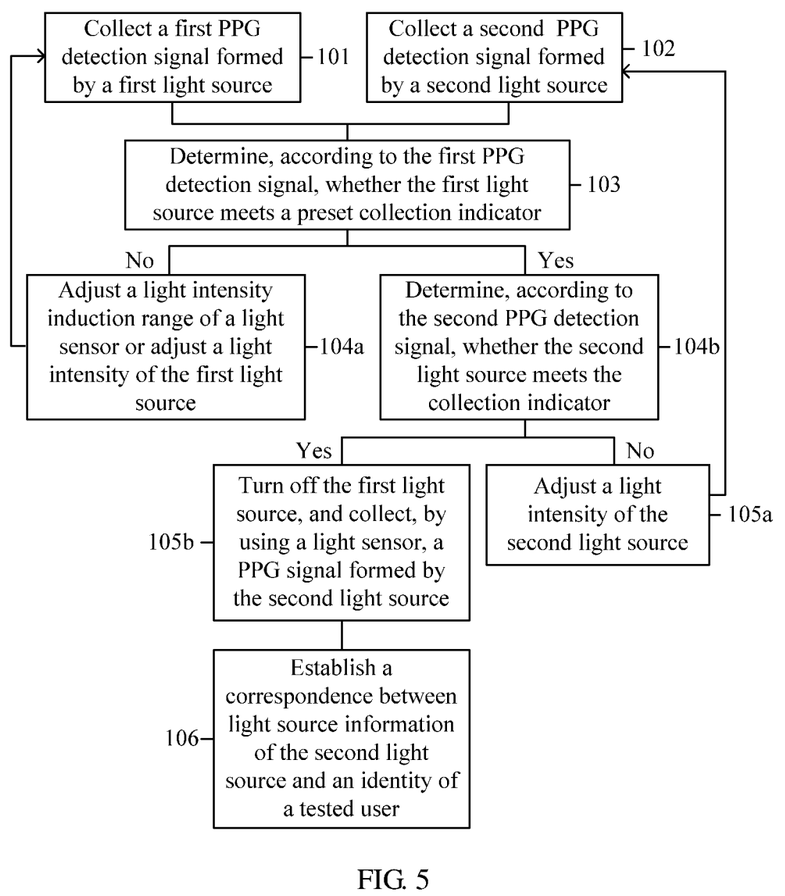
FIG. 5 is a schematic flowchart 1 of a PPG signal collection method according to an embodiment of the present invention.

Specifically, based on the PPG signal collection method and the collection apparatus 100 shown in FIG. 1 to FIG. 4, an embodiment of the present invention provides a PPG signal collection method, as shown in FIG. 5, including the following steps.

101: A collection apparatus collects, by using a light sensor, a first PPG detection signal formed by a first light source, where the first light source is a green light source or a blue light source.

Specifically, a default initial light source and a default light intensity sensing range of the light sensor are pre-stored inside the collection apparatus. In this embodiment of the present invention, the initial light source may be set to the first light source (that is, the green light source or the blue light source) of a particular light intensity. The light intensity sensing range is (X, Y), where 0≤X<Y, X is a minimum light intensity value that can be sensed by the light sensor, and Y is a maximum light intensity value that can be sensed by the light sensor.

When a tested user collects a PPG signal by using the collection apparatus (for example, a wearable wristband) for the first time, the default initial light source and the default light intensity sensing range of the light sensor may first be used to collect a PPG signal. However, the default light intensity sensing range of the light sensor and the default initial light source may not ensure that a PPG signal of relatively good signal quality can be collected for the tested user.

Therefore, in step 101, the collection apparatus may first collect, by using the light sensor, the first PPG detection signal formed by the default first light source, to determine, according to the first PPG detection signal, whether the currently used first light source can be used to collect a PPG signal of relatively good signal quality for the tested user.

The light intensity sensing range indicates a light intensity interval that can be sensed by the light sensor during a process of collecting a PPG signal. For example, the light intensity sensing range is (0, 1000), and a unit of the light intensity is cd, that is, candela. Certainly, a maximum value of the light intensity sensing range should be less than the maximum light intensity that can be sensed by the light sensor.

102: The collection apparatus collects, by using the light sensor, a second PPG detection signal formed by a second light source, where the second light source is a red light source or an infrared light source.

Similar to step 101, because multiple light sources, such as the first light source and the second light source, are disposed in the collection apparatus, to determine whether the second light source can be used to collect a PPG signal of relatively good signal quality for the tested user, the collection apparatus further needs to collect, by using the sensor, the second PPG detection signal formed by the second light source. In this case, a light intensity of the second light source is a default light intensity pre-stored in the collection apparatus.

Figure 6:
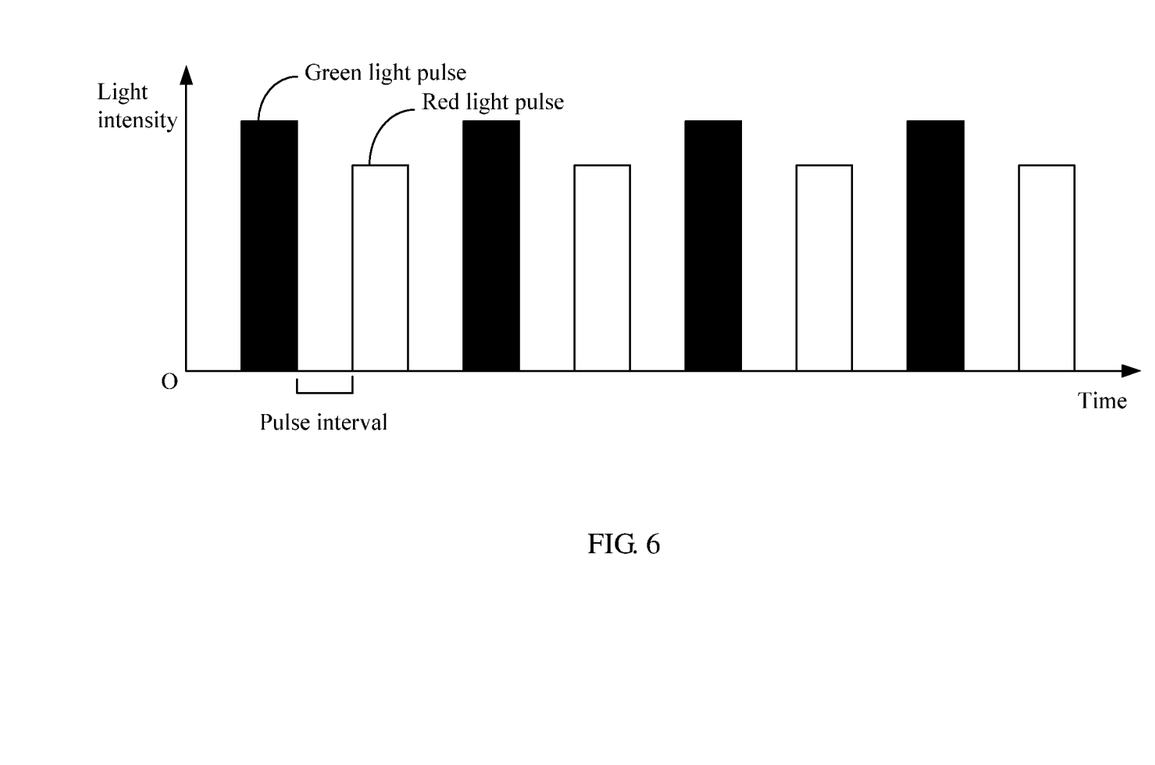
FIG. 6 is a schematic principle diagram of PPG detection signal collection according to an embodiment of the present invention.

For example, steps 101 and 102 may be performed simultaneously. Specifically, as shown in FIG. 6, the first light source being the green light source and the second light source being the red light source are used as an example. Within a detection period, the green light source and the red light source may be turned on in sequence in a pulse manner, so that the light sensor collects a light intensity value of the green light source at each green light pulse moment, and collects a light intensity value of the red light source at each red light pulse moment. Further, the light intensity values collected at different green light pulse moments within the detection period may be used as the first PPG detection signal, and the light intensity values collected at different red light pulse moments within the detection period may be used as the second PPG detection signal.

To ensure accuracy of the first PPG detection signal and the second PPG detection signal, the detection period may be set to at least two heartbeat periods of the tested user.

Certainly, step 101 may be performed before step 102, or step 102 may be performed before step 101, to obtain the first PPG detection signal and the second PPG detection signal. Alternatively, step 101 may first be performed, then step 103 is performed, and when it is determined that the first light source meets a collection indicator, step 102 is performed. This is not limited in this embodiment of the present invention.

In addition, referring to the collection apparatus shown in FIG. 1, in steps 101 to 102, specifically, the light sensor 03 may collect the first PPG detection signal formed by the first light source 01 and the second PPG detection signal formed by the second light source 02.

103: The collection apparatus determines, according to the first PPG detection signal, whether the first light source meets a preset collection indicator.

Specifically, a method for determining whether the first light source meets the preset collection indicator specifically includes the following method A and method B.

Method A: Signal quality of a PPG signal largely depends on a signal-to-noise ratio of the PPG signal. That is, a greater signal-to-noise ratio of the PPG signal indicates higher signal quality of the PPG signal. Therefore, a collection indicator may be preset in the collection apparatus. For example, the collection indicator is a signal-to-noise ratio interval. When a signal-to-noise ratio of the first PPG detection signal lies within the signal-to-noise ratio interval, it may be determined that the first light source meets the collection indicator. In other words, the first light source can be used to collect a PPG signal of relatively good signal quality for the tested user. When the signal-to-noise ratio of the first PPG detection signal does not lie within the signal-to-noise ratio interval, it may be determined that the first light source does not meet the collection indicator.

When a frequency domain range of a PPG signal is 0.5 Hz to 40 Hz, the PPG signal is suitable for testing a blood flow pattern in a human body tissue. Therefore, when the signal-to-noise ratio of the first PPG detection signal is determined, a frequency range of the first PPG detection signal may first be calculated, for example, the frequency range is 25.2 Hz to 48 Hz. Further, signals that do not lie within the range of 0.5 Hz to 40 Hz in the frequency range are regarded as noise, and signals within the range of 0.5 Hz to 40 Hz in the frequency range are regarded as useful signals. Then, a ratio of the useful signals to the noise, that is, the signal-to-noise ratio of the first PPG detection signal, is calculated.

Method B: The first PPG detection signal is generally a digital signal, and may be used to indicate a light intensity of a light beam that is reflected by a skin of the tested user after being emitted by the first light source. A light intensity indicated by the first PPG detection signal may also reflect signal quality of a PPG signal. In this case, the collection indicator may be a first light intensity interval. When the light intensity indicated by the first PPG detection signal lies within the first light intensity interval defined by using a first threshold and a second threshold (the first threshold is greater than the second threshold), it may be determined that the first light source meets the collection indicator. In other words, the first light source can be used to collect a PPG signal of relatively good signal quality for the tested user. When the light intensity indicated by the first PPG detection signal does not lie within the first light intensity interval, it may be determined that the first light source does not meet the collection indicator.

Because the first PPG signal reflects light intensity values of the first light source that are sensed by the light sensor at different moments, the light intensity indicated by the first PPG detection signal may be any light intensity value included in the first PPG signal, or may be an average value of all light intensity values in the first PPG signal. FIG. 6 is still used as an example. The light intensity indicated by the first PPG detection signal may be a minimum value among four light intensity values collected at four different green light pulse moments within the detection period, a maximum value among the four light intensity values, or an average value of a sum of the four light intensity values.

Likewise, the light intensity indicated by the second PPG signal may also be any light intensity value included in the second PPG signal, or an average value of all light intensity values in the second PPG signal. This is not limited in this embodiment of the present invention.

Further, in method B, an alternating current component accounts for about only one thousandth of a direct current component in the first PPG detection signal. Therefore, the collection apparatus may further separate the alternating current component from the direct current component in the first PPG detection signal by using a filtering algorithm. In this case, the collection indicator may be a second light intensity interval. Hence, when a light intensity indicated by the separated direct current component lies within the second light intensity interval defined by using a third threshold and a fourth threshold (the third threshold is greater than the fourth threshold), it may be determined that the first light source meets the collection indicator. In other words, the first light source can be used to collect a PPG signal of relatively good signal quality for the tested user. When the light intensity indicated by the first PPG detection signal does not lie within the second light intensity interval, it may be determined that the first light source does not meet the collection indicator.

In addition, method A or method B may further be selected, according to the light intensity indicated by the first PPG detection signal, to determine whether the first light source meets the collection indicator. For example, when the light intensity indicated by the first PPG detection signal is greater than a light intensity threshold, method B may be selected to determine whether the first light source meets the collection indicator. When the light intensity indicated by the first PPG detection signal is less than the light intensity threshold, method A may be selected to determine whether the first light source meets the collection indicator.

Further, if it is determined that the first light source does not meet the collection indicator, step 104*a* is performed; or if it is determined that the first light source meets the collection indicator, step 104*b* is performed.

104*a*: If the first light source does not meet the collection indicator, the collection apparatus adjusts a light intensity sensing range of the light sensor or adjusts a light intensity of the first light source.

Specifically, in step 104*a*, if the first light source does not meet the collection indicator, it means that the light intensity of the first light source used in step 101 is inappropriate, or the light intensity sensing range of the light sensor used in step 101 is inappropriate. Therefore, the collection apparatus may adjust the light intensity sensing range of the light sensor, or adjust the light intensity of the first light source, until the first light source meets the collection indicator. Then step 104*b* is performed.

Method A is still used as an example. If the signal-to-noise ratio of the first PPG detection signal does not lie within the signal-to-noise ratio interval, in other words, it is determined that the first light source does not meet the collection indicator, the collection apparatus may adjust the light intensity of the first light source according to a relationship between a signal-to-noise ratio of a PPG signal (both the first PPG detection signal and the second PPG detection signal are PPG signals) and a light intensity shown in FIG. 7, and repeatedly perform steps 101 and 103, until the signal-to-noise ratio of the collected first PPG detection signal lies within the signal-to-noise ratio interval. Then step 104*b* is performed.

Figure 7:
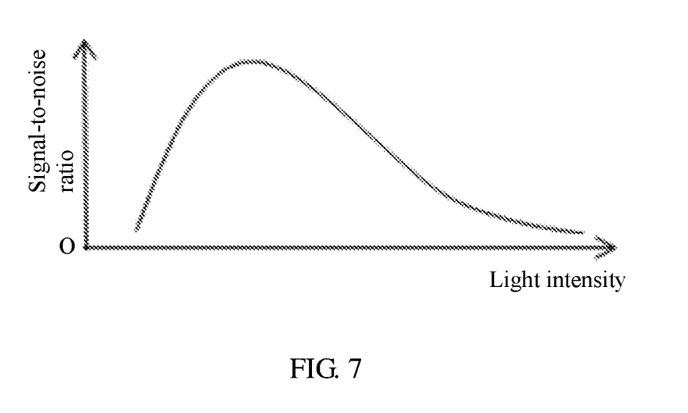
FIG. 7 is a schematic diagram of a variation relationship between a signal-to-noise ratio of a PPG signal and a light intensity.

The signal-to-noise ratio of the first PPG detection signal may be specifically a signal-to-noise ratio of the alternating current component in the first PPG detection signal.

Alternatively, method B is still used as an example. When the light intensity indicated by the first PPG detection signal does not lie between the first threshold and the second threshold, it may be determined that the first light source does not meet the collection indicator. In this case, if the light intensity indicated by the first PPG detection signal reaches the first threshold, it means that the first PPG detection signal already makes the light sensor reach a saturated state. At this time, the maximum value Y of the light intensity sensing range may be increased, and then steps 101 and 103 are repeatedly performed, until the light intensity indicated by the collected first PPG detection signal lies between the first threshold and the second threshold. Correspondingly, if the light intensity indicated by the first PPG detection signal reaches the second threshold, the minimum value X of the light intensity sensing range may be decreased, and steps 101 and 103 are repeatedly performed, until the light intensity indicated by the collected first PPG detection signal lies between the first threshold and the second threshold. Then step 104b is performed.

Certainly, if all the light intensities indicated by the collected first PPG detection signals do not lie within the first light intensity interval after the light intensity sensing range of the light sensor is adjusted according to method B, or if all the signal-to-noise ratios of the collected first PPG detection signals do not lie within the signal-to-noise ratio interval after the light intensity of the first light source is adjusted according to method A, it means that the collection apparatus cannot collect a PPG signal of relatively good signal quality by using the first light source. In addition, an application scope of the first light source in PPG signal collection is wider than an application scope of the second light source in PPG signal collection. Therefore, the second light source cannot be used as a light source of the collection apparatus for PPG signal collection, either. In this case, the collection apparatus may turn off all the light sources and turn off a PPG signal collection function.

104b: If the first light source meets the collection indicator, the collection apparatus determines, according to the second PPG detection signal, whether the second light source meets the collection indicator.

If the first light source meets the collection indicator, it means that the current first light source can be used to collect a PPG signal of relatively good signal quality for the tested user. In this case, if the first light source continues to be used to collect a PPG signal, it can be ensured that signal quality of the collected PPG signal is relatively high, but power consumption of the collection apparatus is relatively high when the first light source is used to collect a PPG signal. Therefore, in step 104b, when the first light source meets the collection indicator, the collection apparatus determines, according to the second PPG detection signal obtained in step 102, whether the second light source that consumes less power meets the collection indicator. If the second light source meets the collection indicator, the first light source may be turned off, and the second light source may be used to collect a PPG signal. In this way, while ensuring that the signal quality of the collected PPG signal is relatively high, the second light source that consumes less power may be used as far as possible to collect a PPG signal, to reduce power consumption of the collection apparatus.

Likewise, a method for determining, according to the second PPG detection signal, whether the second light source meets the collection indicator is similar to method A in step 103, that is, a signal-to-noise ratio of the second PPG detection signal is calculated. If the signal-to-noise ratio of the second PPG detection signal lies within the signal-to-noise ratio interval, it may be determined that the second light source meets the collection indicator. In other words, the second light source can be used to collect a PPG signal of relatively good signal quality for the tested user. When the signal-to-noise ratio of the second PPG detection signal does not lie within the signal-to-noise ratio interval, it may be determined that the second light source does not meet the collection indicator.

The first light source and the second light source use a same light sensor, and when it is determined in step 104a that the first light source meets the collection indicator, the light intensity sensing range of the light sensor is also determined at the same time. Therefore, when determining whether the second light source meets the collection indicator, the collection apparatus does not need to determine whether the light intensity indicated by the second PPG detection signal lies within the first light intensity interval.

Further, if the second light source does not meet the collection indicator, step 105a is performed; or if the second light source meets the collection indicator, step 105b is performed.

105a: If the second light source does not meet the collection indicator, the collection apparatus adjusts a light intensity of the second light source, until a signal-to-noise ratio of the second PPG detection signal lies within the signal-to-noise ratio interval.

Because the light intensity sensing range of the light sensor has been determined, in step 105a, if the second light source does not meet the collection indicator, it means that the light intensity of the second light source used in step 102 (that is, the default light intensity used in step 102) is inappropriate. In this case, the collection apparatus may adjust the light intensity of the second light source, until the second light source meets the collection indicator. Then step 105b is performed.

Specifically, if it is determined that the second light source does not meet the collection indicator, that is, the signal-to-noise ratio of the second PPG detection signal does not lie within the signal-to-noise ratio interval, the collection apparatus may still adjust the light intensity of the second light source according to the relationship between a signal-to-noise ratio of a PPG signal and a light intensity shown in FIG. 7, and repeatedly perform steps 102 and 104b, until the signal-to-noise ratio of the second PPG detection signal lies within the signal-to-noise ratio interval. Then step 105b is performed.

Certainly, it is possible that the signal-to-noise ratio of the collected second PPG detection signal cannot lie within the signal-to-noise ratio interval no matter how the light intensity of the second light source is adjusted. This means: Although less power is consumed by the second light source, the second light source cannot meet the collection indicator, that is, the collection apparatus cannot collect a PPG signal of relatively good signal quality by using the second light source. On the other hand, the first light source that meets the collection indicator has been determined in step 104b. Therefore, in this case, the collection apparatus may continue to use the first light source that meets the collection indicator to collect a PPG signal.

105b: If the second light source meets the collection indicator, the collection apparatus turns off the first light source, and collects, by using the light sensor, a PPG signal formed by the second light source.

If the second light source meets the collection indicator, it means that the current second light source can be used to collect a PPG signal of relatively good signal quality for the tested user. In this case, both the first light source and the second light source may be used to collect a PPG of relatively good signal quality for the tested user. In this case, to reduce power consumption of the collection apparatus, the first light source may be turned off, and the PPG signal formed by the second light source may be collected by using the light sensor.

106: The collection apparatus establishes a correspondence between light source information of the second light source and an identity of a tested user, for the light sensor to subsequently collect a PPG signal for the tested user according to the light source information of the second light source.

The second light source that consumes less power and can provide a PPG signal of relatively good signal quality has been determined in step 105b. Therefore, to allow the tested user to directly use the second light source to collect a PPG signal subsequently, in step 106, the light intensity of the second light source and the determined light intensity sensing range of the light sensor may be stored as the light source information of the second light source, and the correspondence between the light source information of the second light source and the identity (for example, a user account) of the tested user may then be established.

In this way, when the tested user collects a PPG signal by using the collection apparatus again, the collection apparatus may query, according to the correspondence, the light source information of the second light source corresponding to the identity of the tested user, and then set the light intensity of the second light source and the light intensity sensing range of the light sensor directly according to the light source information of the second light source, and collect the PPG signal for the tested user. This greatly shortens a time consumed in PPG signal collection.

It should be noted that, when the tested user subsequently collects a PPG signal by using the collection apparatus again, a method described in steps 101 to 107 may also be used to determine an appropriate light source for the user. This is not limited in this embodiment of the present invention.

In addition, as described in step 105*a*, when the second light source does not meet the collection indicator, that is, the collection apparatus cannot collect a PPG signal of relatively good signal quality by using the second light source, the collection apparatus may continue to collect a PPG signal by using the first light source that meets the collection indicator and that is determined in step 104*b*.

In this case, similar to step 106, a correspondence between light source information of the first light source and an identity of a tested user may further be established, for the light sensor to subsequently collect a PPG signal for the tested user according to the light source information of the first light source. Likewise, the light source information of the first light source includes the light intensity of the first light source and the light intensity sensing range of the light sensor.

In addition, referring to the collection apparatus shown in FIG. 1, steps 103 to 106 that are performed by the collection apparatus may be implemented through executing corresponding program instructions stored in the memory 04 by the processor 05.

Further, when the collection apparatus collects a PPG signal, a light intensity of ambient light exerts great impact on signal quality of the collected PPG signal. This is because: When the first light source or the second light source emits a light beam, ambient light of a larger light intensity causes noise pollution to the light beam, thereby affecting signal quality of a PPG signal collected by the light sensor. Therefore, in the collection apparatus, such as a wearable watch, the light source and the light sensor are generally disposed in positions near a skin of a tested user. After the tested user wears the collection apparatus, the light source can directly touch the skin, and this prevents too much ambient light from reaching the light sensor.

Figure 8:
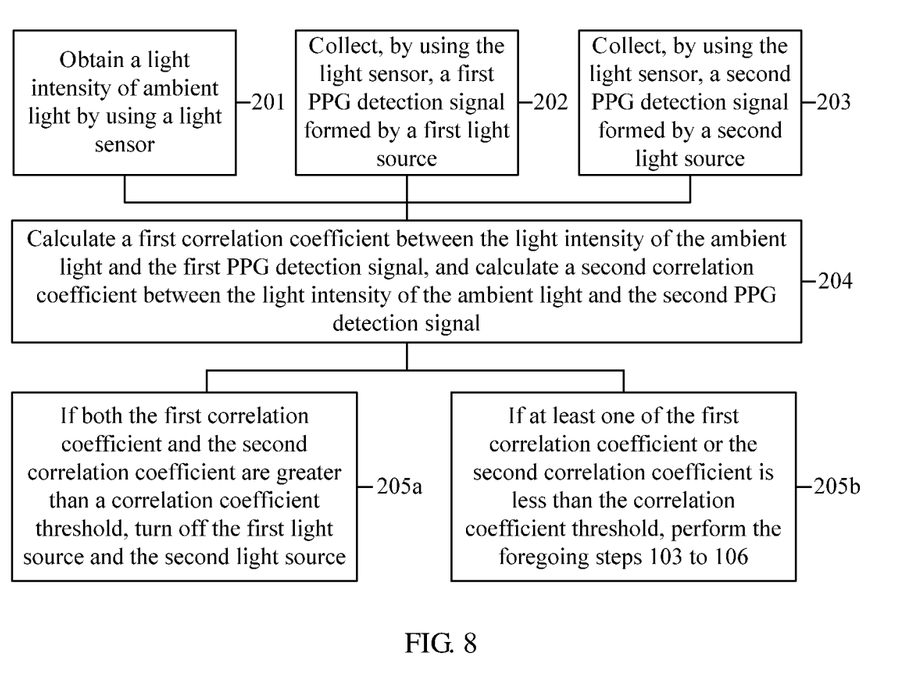
FIG. 8 is a schematic flowchart 2 of a PPG signal collection method according to an embodiment of the present invention.

Based on the foregoing principle, to further reduce power consumption of the collection apparatus and improve the signal quality of the collected PPG signal, an embodiment of the present invention provides a PPG signal collection method, as shown in FIG. 8, including the following steps.

201: A collection apparatus obtains a light intensity of ambient light by using a light sensor.

202: The collection apparatus collects, by using the light sensor, a first PPG detection signal formed by a first light source, where the first light source is a green light source or a blue light source.

203: The collection apparatus collects, by using the light sensor, a second PPG detection signal formed by a second light source, where the second light source is a red light source or an infrared light source.

The collection apparatus may perform steps 201 to 203 simultaneously. Specifically, reference may be made to a related description of FIG. 6 in step 102. The first light source being green light and the second light source being red light are still used as an example. The green light source and the red light source may be turned on in sequence in a pulse manner. Different from step 102, in this case, in addition to collecting a green light intensity at each green light pulse moment and a red light intensity at each red light pulse moment, the light sensor may also collect a light intensity of the ambient light within a pulse interval between every two pulses. Further, the collection apparatus may calculate an average green light intensity, an average red light intensity, and an average ambient light intensity within the detection period, and use the average green light intensity as the first PPG detection signal, use the average red light intensity as the second PPG detection signal, and use the average ambient light intensity as the light intensity of the ambient light obtained in step 201.

In this way, the collection apparatus may obtain the light intensity of the ambient light, the first PPG detection signal, and the second PPG detection signal at the same time, and further select an appropriate light source for a tested user according to the light intensity of the ambient light, the first PPG detection signal, and the second PPG detection signal, thereby shortening a time for selecting the appropriate light source.

In addition, referring to the collection apparatus shown in FIG. 1, step 201 that is performed by the collection apparatus may be specifically: The light sensor 03 obtains the light intensity of the ambient light.

204: The collection apparatus calculates a first correlation coefficient between the light intensity of the ambient light and the first PPG detection signal, and calculates a second correlation coefficient between the light intensity of the ambient light and the second PPG detection signal.

When the light intensity of the ambient light is relatively large, noise pollution is caused to a light beam emitted by the first light source or the second light source, thereby affecting signal quality of a PPG signal collected by the light sensor. A correlation coefficient between the light intensity of the ambient light and a PPG detection signal may reflect a degree of the noise pollution. Generally, a higher correlation coefficient indicates more serious noise pollution, and a lower correlation coefficient indicates less noise pollution.

Specifically, the first light source is used as an example. The following formula may be used to calculate a correlation coefficient r between the light beam emitted by the first light source and the ambient light. The formula is as follows:

$$r = \frac{\sum_{i=1}^{n}(x_i - \bar{x})(y_i - \bar{y})}{\sqrt{\sum_{i=1}^{n}(x_i - \bar{x})\sum_{i=1}^{n}(y_i - \bar{y})^2}}$$

where $x_i$ is a light intensity value absorbed by an optical detector when the first light source is turned on at the $i^{th}$ moment within the detection period, x is an average value of n values of $x_i$ within the detection period, $y_i$ is a light intensity value (that is, a light intensity value of the ambient light) absorbed by the optical detector when the first light source is turned off after the first light source is turned on at the $i^{th}$ moment, and Y is an average value of n values of $y_i$.

Generally, when the light intensity of the ambient light is relatively large, there is a very high probability that noise pollution occurs. Therefore, the collection apparatus may first determine, according to the light intensity of the ambient light, whether the first correlation coefficient and the second correlation coefficient need to be calculated. For example, when the light intensity of the ambient light is greater than a light intensity threshold of the ambient light, the probability that noise pollution occurs is nearly 100%. Therefore, at this time, the collection apparatus may directly turn off a PPG signal collection function. When the light intensity of the ambient light is less than the light intensity threshold of the ambient light, the collection apparatus may calculate the first correlation coefficient between the light intensity of the ambient light and the first PPG detection signal, and the second correlation coefficient between the light intensity of the ambient light and the second PPG detection signal. When the first correlation coefficient and the second correlation coefficient are small, the PPG signal collection function described in steps 103 to 106 is triggered, thereby ensuring the signal quality of the PPG signal collected by the light sensor.

205a: If both the first correlation coefficient and the second correlation coefficient are greater than a correlation coefficient threshold, the collection apparatus turns off the first light source and the second light source.

Specifically, in step 205a, if both the first correlation coefficient and the second correlation coefficient are greater than the correlation coefficient threshold, it means that both the light beams emitted by the first light source and the second light source are polluted by the ambient light. In this case, the signal quality of the collected PPG signal is relatively poor. Therefore, to reduce power consumption of the collection apparatus, the first light source and the second light source may be turned off, and the PPG signal collection function may be turned off.

205b: If at least one of the first correlation coefficient or the second correlation coefficient is less than the correlation coefficient threshold, the collection apparatus performs steps 103 to 106.

Correspondingly, in step 205b, if at least one of the first correlation coefficient or the second correlation coefficient is less than the correlation coefficient threshold, it means that the light beam emitted by at least one of the first light source or the second light source is not polluted by the ambient light. Therefore, the light source not polluted by the ambient light may be used to collect a PPG signal by following steps 103 to 106. For details about a method for collecting a PPG signal, reference may be made to related descriptions in steps 103 to 106, and details are not repeated herein.

In addition, referring to the collection apparatus shown in FIG. 1, steps 202 to 205a (or 202 to 205b) that are performed by the collection apparatus may be implemented through executing corresponding program instructions stored in the memory 04 by the processor 05.

In conclusion, the embodiments of the present invention provide the PPG signal collection method and collection apparatus. The collection apparatus first collects the first PPG detection signal formed by the first light source (that is, the green light source or the blue light source) and the second PPG detection signal formed by the second light source (that is, the red light source or the infrared light source). Further, because the application scope is relatively wide when the green light source is used to collect the PPG signal, the collection apparatus may first determine, according to the first PPG detection signal, the first light source that meets the collection indicator, that is, first ensure that the first light source can provide the PPG signal of relatively good signal quality for the tested user. Further, when the first light source meets the collection indicator, the collection apparatus determines, according to the second PPG detection signal, whether the second light source meets the collection indicator, that is, determines whether the red light source or the infrared light source can provide the PPG signal of relatively good signal quality. If the second light source meets the collection indicator, it means that the second light source is also applicable to the PPG signal collection process. In this case, to reduce power consumption of the collection apparatus, the first light source may be turned off, and the PPG signal formed by the second light source that consumes less power may be collected by using the light sensor. In this way, power consumption in PPG signal collection is reduced while the signal quality of the PPG signal is ensured.

It may be clearly understood by a person skilled in the art that, for the purpose of convenient and brief description, division of the foregoing functional modules is taken as an example for illustration. In actual application, the foregoing functions can be allocated to different functional modules and implemented according to a requirement, that is, an inner structure of an apparatus is divided into different functional modules to implement all or some of the functions described above. For a detailed working process of the foregoing system, apparatus, and unit, reference may be made to a corresponding process in the foregoing method embodiments, and details are not described herein again.

In the several embodiments provided in this application, it should be understood that the disclosed system, apparatus, and method may be implemented in other manners. For example, the described apparatus embodiment is merely an example. For example, the module or unit division is merely logical function division and may be other division in actual implementation. For example, multiple units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electronic, mechanical, or other forms.

The units described as separate parts may or may not be physically separate, and parts displayed as units may or may not be physical units, may be located in one position, or may be distributed on multiple network units. Some or all of the units may be selected according to actual requirements to achieve the objectives of the solutions of the embodiments.

In addition, functional units in the embodiments of the present invention may be integrated into one processing unit, or each of the units may exist alone physically, or two or more units are integrated into one unit. The integrated unit may be implemented in a form of hardware, or may be implemented in a form of a software functional unit.

When the integrated unit is implemented in the form of a software functional unit and sold or used as an independent product, the integrated unit may be stored in a computer-readable storage medium. Based on such an understanding, the technical solutions of the present invention essentially, or the part contributing to the prior art, or all or some of the technical solutions may be implemented in the form of a software product. The software product is stored in a storage medium and includes several instructions for instructing a computer device (which may be a personal computer, a server, a network device, or the like) or a processor (processor) to perform all or some of the steps of the methods described in the embodiments of the present invention. The foregoing storage medium includes any medium that can store program code, such as a USB flash drive, a removable hard disk, a read-only memory (ROM, Read-Only Memory), a random access memory (RAM, Random Access Memory), a magnetic disk, or an optical disc.

The foregoing descriptions are merely specific implementations of the present invention, but are not intended to limit the protection scope of the present invention. Any variation or replacement readily figured out by a person skilled in the art within the technical scope disclosed in the present invention shall fall within the protection scope of the present invention. Therefore, the protection scope of the present invention shall be subject to the protection scope of the claims.

What is claimed is:

1. A method, comprising:
   collecting, by a light sensor, a first photoplethysmography (PPG) detection signal from first light source, wherein the first light source is a green light source or a blue light source;
   collecting, by the light sensor, a second PPG detection signal from a second light source, wherein the second light source is a red light source or an infrared light source;
   determining, according to the first PPG detection signal, whether the first light source meets a preset collection indicator;
   determining, according to the second PPG detection signal, whether the second light source meets the preset collection indicator when the first light source meets the preset collection indicator;
   collecting, by the light sensor, a PPG signal from the second light source when the second light source meets the preset collection indicator; and
   establishing a correspondence between light source information of the second light source and an identity of a tested user.

2. The method according to claim 1, wherein a light intensity sensing range of the light sensor is (X, Y), wherein $0 \leq X < Y$, wherein X is a minimum light intensity value that can be sensed by the light sensor, and wherein Y is a maximum light intensity value that can be sensed by the light sensor; and wherein determining, according to the first PPG detection signal, whether the first light source meets the preset collection indicator comprises:
   determining that the first light source meets the preset collection indicator when a light intensity indicated by the first PPG detection signal is between a first threshold and a second threshold, wherein the first threshold is greater than the second threshold.

3. The method according to claim 2, wherein the method further comprises:
   when the light intensity indicated by the first PPG detection signal reaches the first threshold and the first light source does not meet the preset collection indicator, increasing a maximum value Y of the light intensity sensing range until the light intensity indicated by the first PPG detection signal is between the first threshold and the second threshold.

4. The method according to claim 2, wherein the method further comprises:
   when the light intensity indicated by the first PPG detection signal reaches the second threshold and the first light source does not meet the preset collection indicator, decreasing a minimum value X of the light intensity sensing range until the light intensity indicated by the first PPG detection signal is between the first threshold and the second threshold.

5. The method according to claim 1, wherein determining, according to the first PPG detection signal, whether the first light source meets the preset collection indicator comprises:
   calculating a signal-to-noise ratio of the first PPG detection signal; and
   determining that the first light source meets the preset collection indicator when the signal-to-noise ratio of the first PPG detection signal is within a preset signal-to-noise ratio interval.

6. The method according to claim 5, wherein after calculating the signal-to-noise ratio of the first PPG detection signal, the method further comprises:
   when the signal-to-noise ratio of the first PPG detection signal is not within the preset signal-to-noise ratio interval, adjusting a light intensity of the first light source until the signal-to-noise ratio of the first PPG detection signal is within the preset signal-to-noise ratio interval.

7. The method according to claim 1, wherein determining, according to the second PPG detection signal, whether the second light source meets the preset collection indicator comprises:
   calculating a signal-to-noise ratio of the second PPG detection signal; and
   determining that the second light source meets the preset collection indicator when the signal-to-noise ratio of the second PPG detection signal is within a preset signal-to-noise ratio interval.

8. The method according to claim 7, wherein after calculating the signal-to-noise ratio of the second PPG detection signal, the method further comprises:
   when the signal-to-noise ratio of the second PPG detection signal is not within the preset signal-to-noise ratio interval, adjusting a light intensity of the second light source until the signal-to-noise ratio of the second PPG detection signal is within the preset signal-to-noise ratio interval.

9. The method according to claim 1, wherein before determining, according to the first PPG detection signal, whether the first light source meets the preset collection indicator, the method further comprises:
   obtaining a light intensity of ambient light;
   calculating a first correlation coefficient between the light intensity of the ambient light and the first PPG detection signal;
   calculating a second correlation coefficient between the light intensity of the ambient light and the second PPG detection signal; and
   when both the first correlation coefficient and the second correlation coefficient are greater than a correlation coefficient threshold, turning off the first light source and the second light source.

10. The method according to claim 1,
wherein the light source information of the second light source comprises a light intensity of the second light source and a light intensity sensing range of the light sensor.

11. An apparatus, comprising:
a processor;
a light sensor connected to the processor, wherein the light sensor is configured to:
  collect a first photoplethysmography (PPG) detection signal from a first light source, wherein the first light source is a green light source or a blue light source; and
  collect a second PPG detection signal from a second light source, wherein the second light source is a red light source or an infrared light source; and
a non-transitory computer-readable storage medium storing a program to be executed by the processor, the program including instructions to:
  determine, according to the first PPG detection signal, whether the first light source meets a preset collection indicator;
  determine, according to the second PPG detection signal, whether the second light source meets the preset collection indicator when the first light source meets the preset collection indicator;
  instruct the light sensor to collect a PPG signal from the second light source when the second light source meets the preset collection indicator; and
  establish a correspondence between light source information of the second light source and an identity of a tested user.

12. The apparatus according to claim 11, wherein a light intensity sensing range of the light sensor is (X, Y), wherein o≤X<Y, wherein X is a minimum light intensity value that can be sensed by the light sensor, and wherein Y is a maximum light intensity value that can be sensed by the light sensor; and
  the instructions comprise further instructions to determine that the first light source meets the preset collection indicator when a light intensity indicated by the first PPG detection signal is between a first threshold and a second threshold, wherein the first threshold is greater than the second threshold.

13. The apparatus according to claim 12, wherein the instructions comprise further instructions to: when the light intensity indicated by the first PPG detection signal reaches the first threshold and the first light source does not meet the preset collection indicator, increase a maximum value Y of the light intensity sensing range until the light intensity indicated by the first PPG detection signal is between the first threshold and the second threshold.

14. The apparatus according to claim 11, wherein the instructions comprise further instructions to:
  calculate a signal-to-noise ratio of the first PPG detection signal; and
  determine that the first light source meets the preset collection indicator when the signal-to-noise ratio of the first PPG detection signal is within a preset signal-to-noise ratio interval.

15. The apparatus according to claim 14, wherein the instructions comprise further instructions to: when the signal-to-noise ratio of the first PPG detection signal is not within the preset signal-to-noise ratio interval, adjust a light intensity of the first light source until the signal-to-noise ratio of the first PPG detection signal is within the preset signal-to-noise ratio interval.

16. The apparatus according to claim 11, wherein
the instructions comprise further instructions to calculate a signal-to-noise ratio of the second PPG detection signal; and
determine that the second light source meets the preset collection indicator when the signal-to-noise ratio of the second PPG detection signal is within a preset signal-to-noise ratio interval.

17. The apparatus according to claim 16, wherein
the instructions comprise further instructions to: when the signal-to-noise ratio of the second PPG detection signal is not within the preset signal-to-noise ratio interval, adjust a light intensity of the second light source until the signal-to-noise ratio of the second PPG detection signal is within the preset signal-to-noise ratio interval.

18. The apparatus according to claim 11, wherein
the light sensor is further configured to obtain a light intensity of ambient light; and
the instructions comprise further instructions to:
  calculate a first correlation coefficient between the light intensity of the ambient light and the first PPG detection signal;
  calculate a second correlation coefficient between the light intensity of the ambient light and the second PPG detection signal; and
  when both the first correlation coefficient and the second correlation coefficient are greater than a correlation coefficient threshold, turn off the first light source and the second light source.

19. The apparatus according to claim 11, wherein the instructions comprise further instructions to:
  save the correspondence to the non-transitory computer-readable storage medium, wherein the light source information of the second light source comprises a light intensity of the second light source and a light intensity sensing range of the light sensor.

20. A computer program product being embodied in a non-transitory computer-readable medium and comprising computer instructions for:
  collecting a first photoplethysmography (PPG) detection signal from a first light source, wherein the first light source is a green light source or a blue light source;
  collecting a second PPG detection signal from a second light source, wherein the second light source is a red light source or an infrared light source;
  determining, according to the first PPG detection signal, whether the first light source meets a preset collection indicator;
  determining, according to the second PPG detection signal, whether the second light source meets the preset collection indicator when the first light source meets the preset collection indicator; and
  collecting a PPG signal from by the second light source when the second light source meets the preset collection indicator; and
  establishing a correspondence between light source information of the second light source and an identity of a tested user.

21. The computer program product according to claim 20, wherein the first PPG detection signal and the second PPG detection signal are collected by a light sensor, wherein a light intensity sensing range of the light sensor is (X, Y), wherein o≤X<Y, wherein X is a minimum light intensity value that can be sensed by the light sensor, and wherein Y is a maximum light intensity value that can be sensed by the light sensor; and the instructions comprise further instructions for determining that the first light source meets the preset collection indicator when a light intensity indicated by the first PPG detection signal is between a first threshold and a second threshold, wherein the first threshold is greater than the second threshold.

22. The computer program product according to claim 20, wherein the instructions comprise further instructions for:
   calculate a signal-to-noise ratio of the first PPG detection signal; and
   determine that the first light source meets the preset collection indicator when the signal-to-noise ratio of the first PPG detection signal is within a preset signal-to-noise ratio interval.

\* \* \* \* \*